United States Patent
Duncan et al.

(10) Patent No.: US 11,878,983 B2
(45) Date of Patent: Jan. 23, 2024

(54) THERMOCHEMICAL TREATMENT OF CELLULOSIC MATERIALS

(71) Applicant: CIRCA GROUP LIMITED, Melbourne (AU)

(72) Inventors: Anthony James Duncan, Brighton (AU); Ebbe Jan Dommisse, Sandringham (AU); Warwick Douglas Raverty, Viewbank (AU)

(73) Assignee: CIRCA GROUP LIMITED, Melbourne (AU)

( * ) Notice: Subject to any disclaimer, the term of this patent is extended or adjusted under 35 U.S.C. 154(b) by 401 days.

(21) Appl. No.: 17/270,274

(22) PCT Filed: Aug. 15, 2019

(86) PCT No.: PCT/AU2019/000096
§ 371 (c)(1),
(2) Date: Feb. 22, 2021

(87) PCT Pub. No.: WO2020/037351
PCT Pub. Date: Feb. 27, 2020

(65) Prior Publication Data
US 2021/0317130 A1 Oct. 14, 2021

(30) Foreign Application Priority Data
Aug. 24, 2018 (AU) .................. 2018903116

(51) Int. Cl.
*C07D 493/08* (2006.01)
*B01J 6/00* (2006.01)

(52) U.S. Cl.
CPC ............ *C07D 493/08* (2013.01); *B01J 6/008* (2013.01)

(58) Field of Classification Search
CPC ................................. B01J 6/008; C07D 493/08
USPC ........................................... 549/397; 201/2.5
See application file for complete search history.

(56) References Cited

U.S. PATENT DOCUMENTS

| 9,376,451 | B1 | 6/2016 | Huber |
| 10,093,638 | B2 | 10/2018 | Masuno |
| 2011/0114876 | A1 | 5/2011 | Brady |
| 2012/0111714 | A1 | 5/2012 | Court |
| 2016/0185794 | A1 | 6/2016 | Huber |

FOREIGN PATENT DOCUMENTS

| CN | 101735282 A | 6/2010 |
| CN | 106928285 A | 7/2017 |
| WO | 2011000030 A1 | 1/2011 |
| WO | 2016039996 A1 | 3/2016 |

OTHER PUBLICATIONS

Kawamoto, H., et al. Catalytic pyrolysis of cellulose in sulfolane with some acidic catalysts. J Wood Sci (2007) 53:127-133.
Shafizadeh, F., et al. Some Reactions of Levoglucosenone. Wood Chemistry Laboratory, Department of Chemistry 59812. Carbohydrate Research, 71 (1979) 169-191.
Energy & Fuels, 2016, 30(10), p. 8009-8018.
Wood preservation, 1996, vol. 22-3, p. 10-16. (Google Translation Provided).
He, J. et al. (2017) Production of levoglucosenone and 5-hydroxymethylfurural from cellulose in polar aprotic solvent-water mixtures, Green Chemistry, vol. 19, pp. 342-3652.

*Primary Examiner* — Jeffrey H Murray
(74) *Attorney, Agent, or Firm* — Volpe Koenig (57) ABSTRACT

A method of producing levoglucosenone from particulate cellulosic material. The method comprises forming a premix of particulate cellulosic material, water, acid and a polar organic solvent. The solvent has a higher boiling point than levoglucosenone. The pre-mix is fed into a pyrolysis reactor, such as a fluidised bed reactor, in which the pre-mix is fluidised by a fluidising gas. The reactor is maintained at a temperature within the range 250° C. to 450° C., and gaseous products and char are withdrawn from the pyrolysis reactor. Levoglucosenone and the polar organic solvent are condensed from the gaseous products, produced by the reactor.

17 Claims, 2 Drawing Sheets

THERMOCHEMICAL TREATMENT OF CELLULOSIC MATERIALS

This application is a national stage entry of International Patent Application No. PCT/AU2019/000096 filed on Aug. 15, 2019 based on Australian Patent Application No. 2018903116 filed Aug. 24, 2018, which applications are incorporated by reference herein as fully set forth.

FIELD OF THE INVENTION

The invention relates to methods of thermochemical treatment of cellulosic materials such as lignocelluloses so that they are converted to a separable mixture of volatile organic compounds, water and char.

BACKGROUND OF THE INVENTION

In this specification, where a document, act or item of knowledge is referred to or discussed, this reference or discussion is not an admission that the document, act or item of knowledge or any combination thereof was at the priority date:
(i) part of the common general knowledge; or
(i) known to be relevant to an attempt to solve any problem with which this specification is concerned.

The great majority of synthetic organic chemicals, including polymers, pharmaceuticals, herbicides, pesticides, dyes, pigments, and liquid transport fuels are derived from crude petroleum from fossil sources. One of the recommended means of reducing emission of greenhouse gases is full, or partial, replacement of petroleum-derived chemicals and polymers with chemicals and polymers derived from renewable resources, such as plantation forestry, agriculture and aquaculture. This replacement would have the additional advantage of reducing the rate of usage of the limited remaining fossil petroleum reserves and permit their exploitation to be restricted to production of the relatively modest number of synthetic organic chemicals that cannot be made cost-effectively from renewable resources. With the exception of limited annual supplies of vegetable oils and fats, most high volume renewable organic materials that can be harvested in a cost-effective manner are non-volatile solids. Many means of converting renewable solid organic materials, that can be harvested in very large quantities, into organic liquids, using thermochemical processing, biochemical processing and/or biological processing, are being actively developed worldwide. Generally the existing means have significant disadvantages for the production of renewable liquid chemicals. These disadvantages include the use of expensive enzymes, the requirement for processing at high pressures, necessitating the use of very large processing facilities with associated high costs associated with transporting bulky renewable organic materials over large collection areas, low net yields of energy, chemical complexity and instability of the liquid products and additional demands for often scarce resources of fresh water.

The present invention seeks to provide an alternative means of enabling renewable organic materials, namely those comprising cellulose, hemicelluloses and lignins—so called "cellulosic materials"—to be converted selectively into useful yields of levoglucosenone that preserve much of the natural asymmetry present in the polysaccharide polymers in the materials without the use of high pressure processing. Levoglucosenone may either be used directly as a chemical intermediate, or may be subjected to further processing into other renewable organic chemicals and polymers.

The term 'cellulosic material' and forms of the term 'cellulosic material' as used in this description includes hemicellulosic and lignocellulosic material generally, and particularly includes any vegetable matter, wood, or wood product, paper, paperboard, or paper product, yarn, textile, or textile product having a combined cellulose and hemicellulose content above 30%. It also includes but is not limited to woodchips, sawdust, twigs, bark, leaves, seed pods and other forest litter, cereal and grass straws and hays, oilseed straws, sugar cane bagasse, banana pseudostem waste, oil palm waste, general garden waste, algal 'cake' derived from aquaculture and other vegetable matter.

Levoglucosenone has been recognized as a valuable chemical product which could be obtained by the pyrolysis of lignocellulosic material for many decades. However, despite its value, to the best of applicant's knowledge, there has been no large scale commercial manufacture until quite recently because of substantial difficulties posed by upscaling laboratory pyrolysis methods to a level where they could be feasible on a large scale production facility. The problems encountered with earlier processes included huge reductions in reaction efficiency when reactions were increased beyond the scale of grams, reactivity of levoglucosenone in pyrolysis conditions, production of tars which "gum up" reaction vessels, and the difficulties of separating levoglucosenone product entrained with the tars.

More recently, a process which is described in International Patent Application PCT/AU2010/000811 (Raverty et al), has proven to be effective for producing kilogram amounts of levoglucosenone by pyrolysing wood pulp in a screw reactor. Whilst this process has proven a major step forward, it is still limited by physical difficulties associated with scaling up screw reactors such that they are able to produce levoglucosenone in quantities measured in tonnes. Screw reactors are difficult to maintain under the harsh conditions encountered during pyrolysis and they are limited in the quantity of product they can produce. Some of the difficulties encountered with screw reactors have included the requirement to operate under reduced pressure, inefficient heat transfer with increasing size, and problems with lubrication to prevent seizing up, and "gumming up" of equipment by tars and other reaction products. There is thus a need for an alternative process which does not have the same limitations as screw reactor pyrolysis.

SUMMARY OF THE INVENTION

The invention provides in one aspect

A method of producing levoglucosenone from particulate cellulosic material comprising,
  forming a premix comprising particulate cellulosic material, water, acid and a polar organic solvent having a higher boiling point than levoglucosenone,
  feeding the pre-mix into a pyrolysis reactor, maintained at a temperature within the range 250° C. to 450° C.,
  withdrawing gaseous products and char from the pyrolysis reactor, and
  condensing levoglucosenone and the polar organic solvent from the gaseous products,
wherein, the pyrolysis reactor comprises a reactor in which the pre-mix is fluidised by a fluidising gas.

The polar organic solvent may be recycled to form further pre-mix.

Suitably, the mixing of the pre-mix components is carried out for a time sufficient to evenly impregnate the cellulosic material. It may be impregnated for a time sufficient to allow the cellulosic material to swell and absorb components in the mix. Water may be added to distribute the water-soluble components more evenly in the pre-mix. A mixer as is known in the art may be used to ensure that all the components are intimately admixed.

Applicants have found that allowing the swelling and absorption to occur for a period of at least 0.5 minutes more preferably 5 minutes can usually lead to adequate swelling of the cellulosic material. This facilitates even absorption of the liquid components of the pre-mix into the swelled cellulosic material.

As the pyrolysis of cellulosic material tends to produce tars which can deposit on the internal walls of vessels and pipes and stop continuous reaction processes by impeding heat exchange and eventually blocking the flow of process streams, it is useful to incorporate solvent materials in the pre-mix. These can help to ameliorate problems associated with tar build up. Polar organic solvents are preferred for this function. In order to assist with downstream separation of solvent from the reaction products of pyrolysis in the pyrolysis reactor, it is preferred that the chosen solvent or solvents has a higher boiling point than the desired reaction products. As the desired reaction product is levoglucosenone, it is preferred that the solvent has a higher boiling point than levoglucosenone. Suitably it will have a boiling point at least 20° C. higher.

Figure 1:
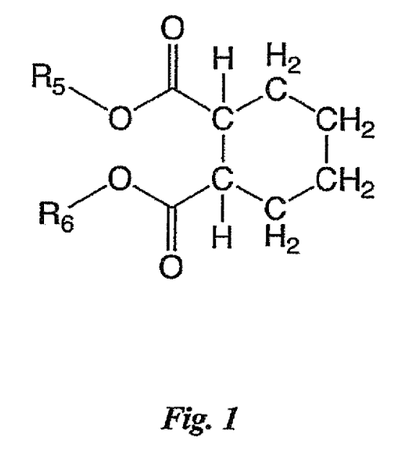
FIG. 1 shows a general formula of a diester.

Examples of suitable solvents include a dialkyl sulfone having the general chemical formula R1-SO2-R2 where R1, and R2 are alkyl groups containing between one and ten carbon atoms, including cyclic sulfones in which R1, and R2 form part of a cyclic polymethylene ring, or a diester of the formula shown in FIG. 1 where R3, and R4 are alkyl groups containing between one and ten carbon atoms, or esters of the formula R5-O—C=O—R6 where R5 is an alkyl group containing between one and ten carbon atoms and R6 is an alkyl group containing between ten and twenty carbon atoms.

In a particular example, the polar organic liquid comprises tetramethylene sulfone.

The pre-mix may comprise the following components each expressed as a weight percentage of dry weight of the cellulosic material:
  water 20%-150% more preferably 20%-100%
  acid 0.1%-10% (preferably phosphoric acid) more preferably 1% to 5% solvent up to 200% more preferably 10%-100%

Whilst there is a huge range of cellulosic materials which may be suitable for the performance of the method of the invention, applicants have found that a particularly suitable cellulosic material is wood in particulate form, such as sawdust. Generally speaking, sawdust having a particle size less than 8 mm and preferably, falling within the range 2 mm to 4 mm can give good performance.

It is anticipated that the method of the invention would be economically more viable if it was carried out on a continuous basis. In order that it can be carried out continuously, the pre-mix may be continuously fed into the pyrolysis reactor. It can be retained in the pyrolysis reactor for sufficient time to pyrolyse the pre-mix to form the products which may be continuously removed. The products may be in the form of two separate streams, namely a gaseous product stream and a solid char stream. This could mean that the reactor would have inlets for the continuous injection of the pre-mix and separate outlets for the char stream and gaseous stream.

Alternatively, the char and gaseous products could be removed through a single outlet. A separator for separating the char and gaseous stream may be provided in such an alternative. A cyclone may be used for this purpose.

Injection of the pre-mix into the reactor may be carried out by any one or more of a vibratory feeder, gravity feeder, screw feeder, conveyor feeder, and/or combinations of these.

The gaseous products may be condensed at different temperatures to provide organic liquid compounds eg. levoglucosenone and furfural as well as water and solvent components of the original pre-mix which may be recycled.

The char may be collected for sale, or it may be combusted, or gasified to provide heat for the pyrolysis reaction and low-oxygen gas for heating and fluidising the thermally stable particulate solid in the pyrolysis reactor. Suitably the particulate solid is unreactive although it may be possible to employ particulate solids which have a catalytic effect eg. solid acidic catalyst.

Alternative or additional heat sources for the pyrolysis reaction may be derived from combustion of gaseous or solid carbonaceous material, electrical heating, microwave heating and/or combinations of these.

To further facilitate rapid reaction, the pre-mix may be preheated prior to injection into the pyrolysis reactor. Preheating may be carried out to reduce the water content of the pre-mix as well. This may occur after the initial swelling. The water content may be reduced to below 100% of the dry weight of the cellulosic material. More preferably it may be reduced below 20%, or it may even be as low as 1%.

Typically, the pre-mix may be preheated to a temperature above 100° C. before being fed into the pyrolysis reactor. It may be fed whilst being entrained with a heated gaseous stream such as steam, nitrogen, carbon dioxide, carbon monoxide or mixtures thereof or other inert gas or even heated oxygen-depleted air.

Whilst it is anticipated that the pyrolysis reaction can be carried out at normal atmospheric pressures, it may also be appropriate in some circumstances to reduce pressures to facilitate drawing off of gaseous products and solid char from the pyrolysis reaction. For example, pressures as low as 30 kPa, or even as low as 10 kPa may be employed.

Generally speaking, a narrower temperature range such as between 300° C. and 400° C. may prove to be particularly efficacious for carrying out the reaction.

Residence times of the pre-mix in the pyrolysis reactor may vary depending on the temperature. However, typically it is expected that residence times less than 1 minute, more preferably, less than 10 or even 2 seconds will be sufficient to give satisfactory yields of materials such as levoglucosone and furfural.

The pyrolysis reactor may comprise a fluidised bed reactor. The fluidised bed may be subjected to a fluidising gas passing through the bed of a thermally stable unreactive particulate solid. It may be chosen from quartz sand, silicon dioxide, diatomaceous earth, kaolinite clay, montmorillonite-smectite clay, illite clay, chlorite clay, haematite, a zeolite, an acid treated char, an acid-treated activated carbon, a metal oxide, an acid-treated metal oxide, a metal sulfate, a metal phosphate, a metal carbonate, a metal-organic framework, and mixtures thereof. The fluidising gas may comprise at least one of flue gas, oxygen-depleted air, nitrogen, carbon dioxide, carbon monoxide and/or a substantially unreactive carrier gas and mixtures of these.

Preferably the pre-mix is subjected to at least one of preheating, dehydration, tumbling in an auger and steam injection prior to injection into the fluidised bed reactor.

Acids which may be suitable for incorporation into the pre-mix may be chosen from $H_3PO_4$, $NaH_2PO_4$, $KH_2PO_4$, $H_2SO_4$, $NaHSO_4$, $KHSO_4$, or a solid acidic catalyst that can act as a fluidising and heat exchange medium in the pyrolysis reactor, and mixtures thereof.

The invention may also provide apparatus for producing levoglucosenone comprising,
- a dryer for receiving and reducing the water content of the cellulosic material and to deliver it by a first feeder to a mixer for combining components of the pre-mix,
- a second feeder arranged to continuously transfer the pre-mix from the mixer vessel and to inject it into a pyrolysis zone of a fluidised bed pyrolysis reactor through a pre-mix inlet,
- a gas inlet configured to introduce a fluidising gas into a fluidised bed of thermally stable unreactive particulate solid in the pyrolysis reactor,
- a heater for maintaining the temperature in the fluidised bed within the range 250° C. to 450° C.,
- an outlet arranged to withdraw a gaseous stream containing entrained char solids from the pyrolysis reactor,
- a separator arranged to separate char solids from the gaseous stream, and at least one fractionating condenser assembly arranged to receive the separate gaseous stream from the separator to separately condense levoglucosenone and the solvent therefrom.

A drier may be provided to pre-dry the pre-mix upstream of the pre-mix inlet.

The pre-mix inlet may also comprise the gas inlet. Alternatively it may be separate from the gas inlet.

The invention will now be further explained by reference to the following drawings and broad and specific examples of performing the method.

BROAD EXAMPLES

Figure 2:
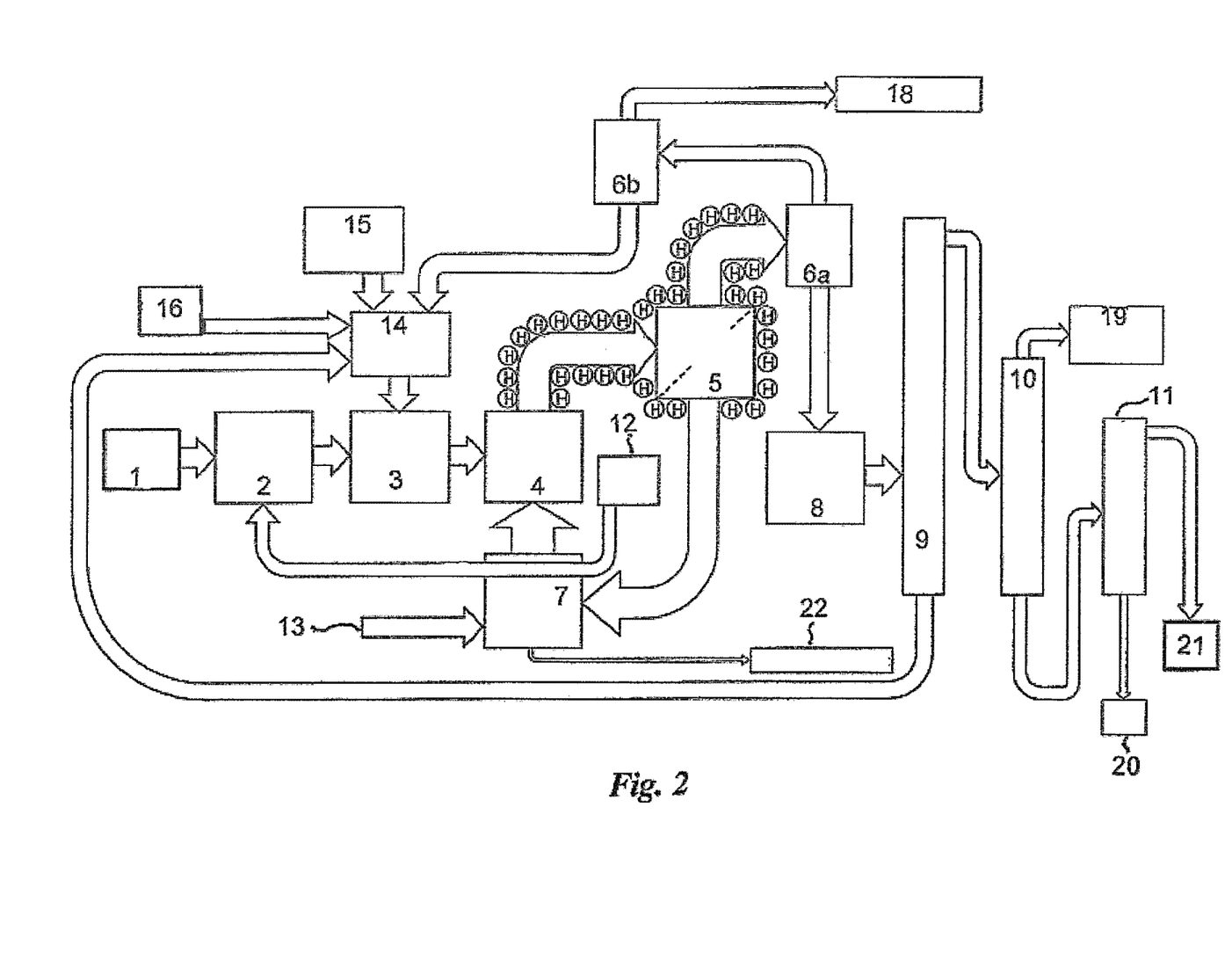
FIG. 2 shows a schematic diagram of an apparatus for producing levoglucosenone.

The broad examples given here are generally directed to treatment of softwood sawdust but, as will be apparent to one skilled in the art, most of the methods are equally applicable to other cellulosic materials, such as waste paper, woodchips, twigs, bark, leaves and other forest litter, cereal and grass straws and hays, oilseed straws, sugar cane bagasse, banana pseudostem waste, oil palm waste, garden waste, algal 'cake' derived from aquaculture or any vegetable material having a significant content of cellulose and/or hemicellulose. FIG. 2 shows a typical flow chart for the steps and equipment required to carry out the method of the invention.

Referring to FIG. 2, the sawdust 1 is first sorted to remove gross contaminants, such as plastics and metal contaminants and is put through a screen, or some other means of removing over-sized particles, to leave a residue of sawdust particles preferably in the range 2-4 mm in size although it will be appreciated that at least some smaller sawdust particles may be included. The mixture of sawdust and swelling catalyst is next passed into a means, such as a drier 2, for evaporating excess water and reducing the water content to a level between 1-25%, preferably between 10-20% by weight of dry sawdust. The dried sorted sawdust is sprayed with a mixture of a polar liquid and strong acid at an impregnation station 3. The polar liquid may comprise water, tetramethylene sulfone ('sulfolane') and a strong acid such as phosphoric acid ($H_3PO_4$) added in amounts between 0.1-10% by weight of dry sawdust, but preferentially between 2.5-5%. Other strong acids, such as sulfuric acid, methanesulfonic acid, trifluoromethanesulfonic acid ('triflic acid'), hydrohalic acids, nitric acid and formic acid may also be employed, but $H_3PO_4$ is preferred in cases where the carbonaceous char is to be used as an agricultural or horticultural fertiliser and a carbon sequestering agent. The polar liquid mixed with strong acid ('swelling catalyst') is sprayed onto the sawdust at rates between 50-500% of the dry weight of sawdust being processed, but preferentially at a rate between 50-100% of the dry weight of sawdust. For other lignocellulosic materials, the proportion of swelling catalyst used must be adjusted so that sufficient is added to swell most of the cellulose and hemicellulose present so that the acid can penetrate the material rapidly.

The dried, heated impregnated sawdust pre-mix is then conveyed at a controlled rate into a fluidised bed reactor 4, by means such as a screw feeder. The fluidised bed 4 contains a thermally stable unreactive particulate solid held at a temperature between 300 and 500 degrees and preferably between 300 and 400 degrees. The outlet of the reactor is directed to a separator 5 for separating gaseous reaction products from entrained solid reaction products under reduced pressure, or at ambient pressure. The separator may comprise a series of heated cyclones. These are connected in turn to one or more condenser heat exchangers 6, capable of cooling the gaseous products to temperatures below 100 degrees. Alternatively, the reactor 4, may be equipped with a separate means for continuously extracting the lower density char by-product from the higher density fluidising thermally stable unreactive particulate solid through a different outlet (not shown). The outlet of the reactor, the cyclones and the condenser heat exchanger 6 may be connected to a means of applying a reduced pressure between 10 and 101 (atmospheric pressure) kPa, but preferentially in the range 30-101 kPa. The reactor 4 is equipped with a means of applying heat in a controlled manner to the fluidised bed such that the pre-mix is heated quickly to a temperature between 300 and 500, but preferentially in the range 300-350 degrees. To provide heat and fluidising gas to the fluidised bed, a char gasifier 7 may be used to combust a proportion of recycled byproduct char with air 13. The resulting syngas is fed into the reactor 4. A steam generator/heat exchanger 12, heated by the gasifier, supplies steam to the sawdust dryer and decreases the temperature of the fluidising gas to a range suitable for maintaining a temperature of 300-350 degrees inside the reactor. Additional combustion gas such as natural gas (not shown) may be added to the gasifier to initiate combustion and to control the temperature. The residence time in the reactor may be in the range 0.01-10 seconds, but preferentially in the range 0.5-1.0 seconds. The gas used to fluidise the fluidised solid desirably has an oxygen content below 0.5% on a volume basis.

The action of heat and the acid on the swollen cellulosic material during its period in the reactor causes dehydration of the anhydrohexose and anhydropentose biopolymers from which the cellulose and hemicelluloses present are made up. Depending on the reaction conditions this can result in formation of levoglucosenone as the major volatile product in molar yields of 10-40%, with smaller amounts of water, furfural, 5-methylfurfural, acetic acid and formic acid. Significant quantities of non-volatile carbonaceous char are also formed by dehydration of the lignin present and by non-selective dehydration of the poly-anhydrohexoses and poly-anhydropentoses present and also, presumably, by further reaction and thermal decomposition of some of the volatile products.

The residence time and temperature must be kept under careful control in order to minimise the undesirable loss of volatile products via the last mentioned mechanism. At the elevated temperature in the fluidised bed pyrolysis reactor the water, sulfolane, levoglucosenone, furfural and other volatile products boil rapidly and the pressure of the resulting vapours assist in mixing unreacted sawdust and carrying the levoglucosenone and other volatile products away from contact with the reactive carbonaceous char and out though the outlet of the fluidised bed reactor. The pressure differential created by the boiling water, sulfolane and volatile dehydration products cause the vapours to be conveyed rapidly through the outlet and into the cyclone 5. If the walls of the cyclone are held at a temperature between 200 and 300 degrees by heaters H, most of the volatile products remain in the vapour phase and separation from the solid carbonaceous char and fluidising solid can be efficient. The carbonaceous char which may contain the $H_3PO_4$ may be preferentially allowed to fall onto the surface of a heat exchanger (not shown) carrying swelling catalyst to the pre-mix sprays, so that the sawdust is sprayed with hot swelling catalyst liquid. After cooling, the carbonaceous char can be conveyed to a storage vessel (not shown), where part of it can be fed to a gasifier 7 to provide heat to maintain the temperature of the fluidised bed and/or to provide an inert hot fluidising gas comprising mainly nitrogen, carbon monoxide and carbon dioxide with small amounts of hydrogen, methane and steam (syngas). The unused part of the carbonaceous char may be used as a renewable fuel, or it may be used as an agricultural or horticultural fertilizer, in which use it also acts as a means of sequestering carbon in the soil.

The applicant has found it useful to pass the vapours containing sulfolane, levoglucosenone, furfural, 5-methyl furfural, acetic acid, formic acid, steam and other volatile pyrolysis by-products through a series of two or more heat exchangers in the condensers 6a and 6b held at different temperatures so that the sulfolane, levoglucosenone and most of the furfural and 5-methyl furfural are condensed in the first heat exchanger (partial condensation) and directed to storage 8. Most of the acetic acid, formic acid and steam are condensed in the second and subsequent heat exchangers 6b (total condensation). A proportion of the secondary condensate from 6b may be recycled to a preparation station 14 where the mixture for impregnation of the sawdust is prepared prior to being directed into the impregnation station 3. The remaining proportion of the secondary condensate is pumped to the secondary condensate storage vessel 19 where it is combined with secondary condensate and the mixture is pumped to an aerobic biological waste water treatment system (not shown) where the organic compounds are converted to carbon dioxide and water. The preparation station 14 has additional inputs from an acid source 15, fresh solvent source 16 and the condensate from 6b and may have input of fresh water (not shown). The applicant has found it beneficial to take the liquid condensate from the first heat exchanger into a first condensate storage vessel 8 and the liquid from the second and subsequent heat exchangers to a second (total) condensate storage vessel (not shown). Non-condensable gases from 6b comprising nitrogen, carbon dioxide, carbon monoxide and traces of hydrogen and methane are piped to an oxidizing flare 18 where it is mixed with air and burnt to convert the carbon monoxide, hydrogen and methane to carbon dioxide and water. The combustion gases from the flare, comprising almost exclusively carbon dioxide and water are vented to atmosphere.

The liquid condensate in the first condensate storage vessel 8 is then pumped to an efficient fractional distillation facility 9, 10, 11 held under a reduced pressure in the range 0.1-10 kPa, but preferentially in the range 1-4 kPa, where levoglucosenone, furfural, water and other minor volatile by-products can be distilled away from the sulfolane and minor less volatile by-products. The liquid solvent (eg. sulfolane), mixed with the less-volatile by-products is then pumped to a storage vessel (not shown) following which it is pumped to preparation station 14 where it is mixed with $H_3PO_4$ in preparation for use as swelling catalyst for further quantities of sawdust. The mixture of water, formic acid, acetic acid, furfural, 5-methyl furfural and levoglucosenone; that distil are collected and pumped to a second fractional distillation column held under a reduced pressure in the range 0.5-10 kPa, but preferentially in the range 0.5-4 kPa, where furfural, water and other minor volatile by-products can be distilled away from the levoglucosenone. The levoglucosenone is then pumped to a storage tank (not shown) from which it is then pumped to a third fractional distillation column 11 held under a reduced pressure in the range 0.5-10 kPa, but preferentially in the range 1-4 kPa, where levoglucosenone can be distilled away at greater than 98% purity from minor less-volatile contaminants formed by partial thermal decomposition of the levoglucosenone to be held in storage facility 21.

The minor volatile products, including furfural, 5-methyl furfural, acetic acid, formic acid and water are pumped to a second condensate storage vessel 19 from where they are pumped to an aerobic biological waste water treatment system (not shown) where the organic compounds are converted to carbon dioxide, water and bacterial biomass. Distillation residues from the second and third distillation columns that include humins and tarry substances, 20, may be combined with the proportion of char that is fed to the gasifier.

Ash from the gasifier 7 may be directed to a storage 22 where it may be prepared for agricultural use.

A number of laboratory tests were carried out on various pre-mixes using Tasmanian *Pinus radiata* (TPR) sawdust and the results are summarised in the following Examples.

SPECIFIC EXAMPLES

Example A

Tasmanian *Pinus* radiata (TPR) sawdust having a particle size predominantly in the range 2 mm to 4 mm was oven dried to a moisture content where it comprised 1.23 g of dry weight sawdust and 0.27 g of water. It was added to a bed of sand pre-heated (electrically) to a temperature of 350° C. under a vacuum of 35 kPa absolute and fluidised with nitrogen. It produced a complex and commercially unattractive mixture of small quantities of acetic acid, 1-hydroxy-2-propanone, hydroxyacetaldehyde, furfural, 1,2-cyclopentanedione, guaiacol, 4-methylguaiacol; 4-vinylguaiacol, isoeugenol and levoglucosan using 1-tetradecane as an internal standard for the gas chromatographic (gc) analysis of products.

Example B

TPR sawdust having a particle size predominantly in the range 2 mm to 4 mm was oven dried to a basis where it comprised 1.23 g of dry weight sawdust and 0.27 g of water.

It was added to the sand bed that had been pre-heated to 500° C. and repeating the procedure of Example A resulted in gc identification of a very similar mixture of the same compounds in even smaller quantities. Owing to the very low yields of volatile products and the complexity of the mixture obtained, no quantitative analysis of volatile products was conducted in Examples A and B.

Example C 4.40 g TPR sawdust on an oven dried basis containing 0.60 g water was mixed and pre-impregnated with a solution of 0.25 g of 85% $H_3PO_4$ dissolved in 5.639 g water.

Following pre-impregnation of the TPR with dilute $H_3PO_4$ to form a pre-mix it was then subjected to the same procedure as described in Example A and the gaseous offtake was condensed to yield:
6.51% yield of levoglucosenone (WO) (w/w on oven-dried wood basis).
0.98% yield of furfural (w/w on oven-dried wood basis),
0.28% yield of 2-butanone (w/w on oven-dried wood basis) and
0.28% yield of acetic acid (w/w on oven-dried wood basis).

The three minor products above are relatively easy to remove from WO using vacuum fractional distillation.

Example D (TPR Sawdust=0.408 g on oven-dried basis containing water=0.0735 g; sulfolane=0.530 g; 85 wt % $H_3PO_4$=0.0204 g; Pressure=35 kPa; Sand Temperature=350° C.) Pre-impregnation of the TPR sawdust dried to 18% moisture content with a mixture of 5% (w/w on oven-dried wood basis) of 85 wt % $H_3PO_4$ dissolved in 139% sulfolane (w/w on oven-dried wood basis), then repeating Example C resulted in a similarly simple mixture of products. The mixture was analysed by gc and found to contain:
5.61% yield of LGO (w/w on oven-dried wood basis),
0.47% yield of furfural (w/w on oven-dried wood basis)
and no detectable amounts of 2-butanone, or acetic acid.

Example E was conducted in duplicate to check the reproducibility of the yields.

Example E1

(TPR Sawdust=0.607 g on oven-dried basis containing water=0.0765 g; sulfolane=0.790 g; 85 wt % $H_3PO_4$=0.0304 g; Pressure=35 kPa; Sand Temperature=320° C.). The sample of TPR sawdust containing 18% moisture used in Example D had all been consumed and a second sample containing 11.2% moisture content was impregnated with a mixture of 5% phosphoric acid and 130% sulfolane and 1.5 g of the impregnated sawdust was allowed to fall into the bed of sand fluidised with nitrogen pre-heated and held at the lower temperature of 320° C.

Example E2

(TPR Sawdust=0.607 g on oven-dried basis containing water=0.0765 g; sulfolane=0.790 g; 85 wt % $H_3PO_4$=0.0304 g; Pressure 35 kPa; Sand Temperature=320° C.) was a duplicate of Example E1.

Ge analysis of the products obtained from Examples E1 and E2 resulted in generation of the following LGO and furfural yield data:

| | Temperature of Sand (° C.) | Pressure inside Fluidised Bed (kPa) | Yield of LGO (w/w % on oven-dried sawdust) | Yield of Furfural (w/w % on oven-dried sawdust) |
|---|---|---|---|---|
| Example E1 | 320 | 35 | 9.01 | 0.85 |
| Example E2 | 320 | 35 | 8.83 | 0.99 |
| Mean Values | | | 8.92 | 0.92 |

The data in the table above indicate that the reproducibility in the LGO yield was of the order of plus/minus 1% of the value obtained whereas that in the furfural yield was plus/minus 8% of the value obtained.

Example F (TPR Sawdust=0.607 g on oven-dried basis containing water=0.0765 g; sulfolane=0.790 g; 85 wt % $H_3PO_4$=0.0304 g; Pressure=35 kPa; Sand Temperature 400° C.) was conducted in the same manner as Examples E1 and E2 except that the temperature of the bed of sand was heated electrically to 400° C. prior to injecting the impregnated sawdust into the fluidised sand. At this higher reaction temperature:
The yield of the LGO (determined as above) decreased to 2.42% (w/w on oven-dried wood basis) and
0.66% of furfural (w/w on oven-dried wood basis) was obtained, together with 0.36% of 2-butanone (w/w on oven-dried wood basis). The higher ratio of furfural to LGO at 400° C. reactor temperature is consistent with the published prior art that reports furfural to be one of the thermal decomposition products of LGO.

Example G (TPR Sawdust=0.607 g on oven-dried basis containing water=0.0765 g; sulfolane=0.790 g; 85 wt % $H_3PO_4$=0.0304 g; Pressure=100 kPa; Sand Temperature=320° C.) was conducted by repeating Example D but increasing the internal pressure within the chamber holding the fluidised sand from 35 kPa (absolute) of nitrogen to 100 kPa (absolute) of nitrogen. In the case of Example G, gc analysis of the condensed volatile products showed the presence of:
7.94% yield of LGO (w/w on oven-dried wood basis),
0.98% yield of furfural (w/w on oven-dried wood basis) and no detectable amounts of 2-butanone, or acetic acid.

Example H (TPR Sawdust 1.23 g on oven-dried basis containing water=0.00 g; sulfolane=0.00 g 85 wt % $H_3PO_4$=0.00 g; Pressure=35 kPa; Zeolite Temperature 350° C.) was conducted in the same manner as Example A with the exception that the sand was replaced with a zeolite and the TPR sawdust used was anhydrous. The zeolite did not fluidise well. The gc analysis of the condensed volatile products from this experiment revealed a completely different product mix from that obtained when sand was used as the fluidised medium. In this case the mixture of volatile products obtained comprised traces of benzene, toluene, ethylbenzene, 1,4-dimethylbenzene, 4-ethyltoluene, trimethylbenzene, indane and other alkylated aromatic compounds. These products have been frequently reported in the prior art when samples of softwoods are pyrolyzed in the presence of zeolites.

In examples I, J, K, L, M, N, O and P below, the flows of fluidising gas were carefully controlled so that the residence times of vapours inside the fluidised bed reactor could be calculated precisely.

Example I (TPR Sawdust=0.607 g on oven-dried basis containing water=0.0765 g; sulfolane=0.790 g; 85 wt % $H_3PO_{49}$=0.0304 g; Pressure=35 kPa; Sand Temperature=320° C., Vapour residence time in the reactor=0.85 seconds).

Example J (TPR Sawdust=0.607 g on oven-dried basis containing water=0.0765 g; sulfolane=0.790 g; 85 wt % $H_3PO_{49}$=0.0304 g; Pressure=35 kPa; Sand Temperature=320° C., Vapour residence time in the reactor=0.85 seconds) was a duplicate of Example I.

Example K (TPR Sawdust=0.607 g on oven-dried basis containing water=0.0765 g; sulfolane=0.790 g; 85 wt % $H_3PO_4$=0.0304 g; Pressure=35 kPa; Sand Temperature 320° C., Vapour residence time in the reactor=0.85 seconds) was a triplicate of Example I.

Example L (TPR Sawdust=0.607 g on oven-dried basis containing water=0.0765 g; sulfolane=0.790 g; 85 wt % $H_3PO_4$=0.0304 g; Pressure=35 kPa; Sand Temperature=320° C., Vapour residence time in the reactor=1.50 seconds) was a duplicate of Example I except that the flow rate of the fluidising gas was reduced so that the residence time of the vapours in the fluidised bed reactor increased to 1.5 seconds to investigate the effect of longer vapour residence times.

Example M (TPR Sawdust=0.607 g on oven-dried basis containing water=0.0765 g; sulfolane=0.790 g; 85 wt % $H_3PO_4$=0.0304 g; Pressure=35 kPa; Sand Temperature=320° C., Vapour residence time in the reactor=1.50 seconds) was a duplicate of Example I except that the flow rate of the fluidising gas was increased so that the residence time of the vapours in the fluidised bed reactor decreased to 0.43 seconds to investigate the effect of shorter vapour residence times.

Example N (TPR Sawdust=0.607 g on oven-dried basis containing water=0.0765 g; sulfolane=0.790 g; 85 wt % $H_3PO_{49}$=0.0304 g; Pressure=35 kPa; Sand Temperature=320° C.) was a duplicate of Example I except that the nitrogen fluidising gas was replaced with a mixture of 10 v/v % $CO_2$, 10 v/v % CO and 80 v/v % $N_2$ to simulate the composition of a flue gas resulting from passage of a limited quantity of air through a bed of char held at a temperature of 900 degrees. Purchase of purified inert gases for fluidising the reactor bed will add to operating costs of the invention and make it less viable economically. The alternative measure of generating low-oxygen fluidising gas by passing air through hot char was therefore simulated as described in the prior art and as shown in Example N and Example 0.

Example O (TPR Sawdust=0.607 g on oven-dried basis containing water=0.0765 g; sulfolane=0.790 g; 85 wt % $H_3PO_4$=0.0304 g; Pressure=35 kPa; Sand Temperature 320° C. was a duplicate of Example N.

Gc analysis of the products obtained from I, J, K, L, M, N and O resulted in generation of the following LGO and furfural yield data:

| | Temperature of Sand (° C.) | Pressure inside fluidised bed (kPa) | Residence time of vapours inside fluidised bed (s) | Composition of fluidising gas (v/v %) | Yield of LGO (w/w % on oven-dried sawdust) | Yield of Furfural (w/w % on oven-dried sawdust) |
|---|---|---|---|---|---|---|
| Example K | 320 | 35 | 0.85 | 100 N2 | 6.72 | 0.99 |
| Example J | 320 | 35 | 0.85 | 100 N2 | 9.19 | 0.29 |
| Example K | 320 | 35 | 0.85 | 100 N2 | 8.79 | 0.75 |
| Example L | 320 | 35 | 1.50 | 100 N2 | 6.85 | 0.92 |
| Example M | 320 | 35 | 0.43 | 100 N2 | 9.03 | 0.91 |
| Example N | 320 | 35 | 0.85 | 10 CO2, 10 CO, 80 N2 | 9.52 | 0.87 |
| Example O | 320 | 35 | 0.85 | 10 CO2, 10 CO, 80 N2 | 8.77 | 0.46 |

The data in the table above indicate that the reproducibility in the LGO yield was again of the order of plus/minus 1% of the value obtained. The data also demonstrate that increasing the residence time of the vapours inside the reactor beyond 1 second results in a significant decrease in the yield of LGO and an increase in the yield of furfural. Furfural is described in the prior art as being one of the products of thermal decomposition of LGO. Changing the composition of the fluidising gas from 100% nitrogen to a mixture of nitrogen with carbon dioxide and carbon monoxide that is typical of the composition of gases described in the prior art formed by passing limited volumes of air through beds of char at 900 degrees does not result in any significant change in the yield of LGO or furfural.

Example J1

(TPR Sawdust=0.607 g on oven-dried basis containing water=0.0765 g; sulfolane=0.3800 g; 85 wt % $H_3PO_{49}$=0.0304 g; Pressure=35 kPa; Sand Temperature=320° C.) was aimed at investigating the effect of reducing the quantity of sulfolane used by 50%.

Example J2

(TPR Sawdust=0.607 g on oven-dried basis containing water=0.0765 g; sulfolane=0.3800 g; 85 wt % $H_3PO_{49}$=0.0304 g; Pressure=35 kPa; Sand Temperature=320° C.) was a duplicate of Example J1.

Example J3

(TPR Sawdust=0.607 g on oven-dried basis containing water=0.0765 g; sulfolane=0.3800 g; 8.5 wt % $H_3PO_{49}$=0.0304 g; Pressure=35 kPa; Sand Temperature=320° C., Vapour residence time in the reactor=0.85 seconds) was a triplicate of Example J1.

Example J4

(TPR Sawdust=0.607 g on oven-dried basis containing water=0.0765 g; sulfolane=0.3800 g; 85 wt % $H_3PO_4$=0.0304 g; Pressure=35 kPa; Sand Temperature=320° C.) was a duplicate of Example J1 except for a change in the addition of the water and $H_3PO_4$ to the sawdust in which the liquid sawdust suspension was subjected to 800 kPa pressure for 5 minutes and then brought back to ambient pressure prior to mixing with sulfolane to investigate the effect of high pressure impregnation of the $H_3PO_4$ into the sawdust.

Example J5

(TPR Sawdust=0.607 g on oven-dried basis containing water=0.0765 g; 85 wt % $H_3PO_{49}$=0.0304 g; Pressure=35 kPa; Sand Temperature=320° C.) was a duplicate of Example J1 except for elimination of all sulfolane from the pre-mix.

Example J6

(TPR Sawdust=0.607 g on oven-dried basis containing water=0.0765 g; 85 wt % $H_3PO_{49}$=0.0304 g; Pressure=35 kPa; Sand Temperature=320° C.) was a duplicate of Example J5 except for a change in the composition of the fluidising gas to mirror Examples N and O above.

Gc analysis of the products obtained from Examples J1, J2, J3, J4, J5 and J6 resulted in generation of the following LGO and furfural yield data:

| | Temperature of Sand (° C.) | Pressure inside fluidised bed (kPa) | Weight % sulfolane added to sawdust) | Composition of fluidising gas (v/v %) | Yield of LGO (w/w % on oven-dried sawdust) | Yield of Furfural (w/w % on oven-dried sawdust) |
|---|---|---|---|---|---|---|
| Mean of Examples J, K & L | 320 | 35 | 130.1 | 100 N2 | 8.47 | 0.68 |
| Example J | 320 | 35 | 62.60 | 100 N2 | 7.24 | 0.48 |
| Example J2 | 320 | 35 | 62.60 | 100 N2 | 8.47 | 0.79 |
| Example J3 | 320 | 35 | 62.60 | 100 N2 | 8.67 | 0.84 |
| Example J4 | 320 | 35 | 62.60 | 100 N2 | 7.95 | 0.89 |
| Example J5 | 320 | 35 | 0.00 | 100 N2 | 5.09 | 0.72 |
| Example J6 | 320 | 35 | 0.00 | 10 CO2 10 CO 80 N2 | 4.87 | 0.90 |

The data in the table above demonstrate that reducing the weight percentage sulfolane added to the sawdust by 50% does not result in a significant decrease in the yield of LGO or a change in the yield of furfural. Alternatively, complete elimination of the sulfolane from the pre-mix results in an undesirable 40% reduction in the yield of LGO and no significant change in the yield of furfural, thereby demonstrating the protective effect of adding a liquid organic solvent to the pre-mix.

Example K1

(TPR Sawdust=0.607 g on oven-dried basis containing water=0.0765 g; sulfolane=0.7900 g; 85 wt % $H_3PO_4$=0.0304 g; Pressure=35 kPa; Sand Temperature=320° C.) was a duplicate of Example 12.

Example K2

(TPR Sawdust=0.607 g on oven-dried basis containing water 0.0765 g; sulfolane=0.7900 g; 85 wt % $H_3PO_4$=0.0304 g; Pressure=35 kPa; Sand Temperature=320° C.) was a duplicate of Example K1 except that the pressure of fluidising gas inside the reactor was increased from 35 kPa to 101 kPa in order to establish whether or not there was any benefit in running the process under vacuum.

Gc analysis of the products obtained from Examples K1 and K2 resulted in generation of the following LGO and furfural yield data:

|  | Temperature of Sand (° C.) | Pressure inside fluidised bed (kPa) | Weight % sulfolane added to sawdust) | Composition of fluidising gas (v/v %) | Yield of LGO (w/w % on oven-dried sawdust) | Yield of Furfural (w/w % on oven-dried sawdust) |
|---|---|---|---|---|---|---|
| Example K1 | 320 | 35 | 130.1 | 100 N2 | 8.00 | 0.27 |
| Example K2 | 320 | 101 | 130.1 | 100 N2 | 9.02 | 0.78 |

The data in the table above demonstrate that increasing the pressure of the fluidising gas and vapours inside the fluidised bed reactor does not result in a significant change in the yield of LGO or a change in the yield of furfural.

The term 'cellulosic material' and forms of the form 'cellulosic material' as used in this description includes hemicellulosic and lignocellulosic material generally, and particularly includes any vegetable matter, wood, or wood product, paper, paperboard, or paper product, yarn, textile, or textile product having a combined cellulose and hemicellulose content above 30%. It also includes but is not limited to woodchips, sawdust, twigs, hark, leaves, seed pods and other forest litter, cereal and grass straws and hays, oilseed straws, sugar cane bagasse, banana pseudostem waste, oil palm waste, general garden waste, algal 'cake' derived from aquaculture and other vegetable matter.

Whilst the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other features.

The reference to any prior art in this specification is not, and should not be taken as, an acknowledgment or any form of suggestion that such prior art forms part of the common general knowledge in Australia.

The invention claimed is:

1. A method of producing levoglucosenone from particulate cellulosic material comprising,
    forming a premix comprising particulate cellulosic material, water, acid and a polar organic solvent having a higher boiling point than levoglucosenone,
    feeding the pre-mix into a pyrolysis reactor, maintained at a temperature within the range 250° C. to 450° C.,
    withdrawing gaseous products and char from the pyrolysis reactor, and
    condensing levoglucosenone and the polar organic solvent from the gaseous products,
    wherein, the pyrolysis reactor comprises a reactor in which the pre-mix is fluidised by a fluidising gas.

2. The method according to claim 1 wherein the cellulosic material is wood in particulate form, and the wood is dried to reduce its water content to less than 100% based on the dry weight of the wood prior to forming the pre-mix.

3. The method according to claim 2 wherein the particulate wood has been dried to a water content between 1% and 25% by dry weight of the particulate wood and the particulate wood has a particle size less than 8 mm.

4. The method according to claim 1 wherein the solvent comprises tetramethylene sulfone.

5. The method according to claim 1 wherein the pre-mix comprises the following components, each expressed as a weight percentage of dry weight of the cellulosic material

| Water | 5% to 150% |
|---|---|
| Acid | 0.05% to 10% |
| Solvent | 10% to 150%. |

6. The method according to claim 5 wherein the pre-mix comprises:

| Water | 20% to 25% |
|---|---|
| Acid | 0.05% to 5% |
| Solvent | 95% to 150% | and wherein the cellulosic material comprises sawdust having a particle size smaller than 8 mm.

7. The method according to claim 1 wherein, the reactor is a fluidised bed reactor, and the pre-mix is continuously injected into and retained in the reactor for sufficient time to pyrolyse the pre-mix to form the gaseous products and char which are both continuously removed from the pyrolysis reactor and separated into a gaseous stream and a char stream.

8. The method according to claim 7 wherein the pyrolysis reactor is a fluidised bed reactor maintained at a temperature between 300° C. and 400° C. provided with an outlet for gaseous products containing entrained char, following which char is separated from the gaseous products to provide a gaseous products stream and a char stream, the gaseous products stream is subjected to fractionation to separate levoglucosenone and the solvent, and the solvent is recycled to be used in preparation of additional pre-mix.

9. The method according to claim 1 wherein the acid is chosen from $H_3PO_4$, $NaH_2PO_4$, $KH_2PO_4$, $H_2SO_4$, $NaHSO_4$, $KHSO_4$, and mixtures thereof.

10. The method according to claim 1 wherein the acid is $H_3PO_4$ or $H_2SO_4$.

11. The method according to claim 1 wherein the pyrolysis reactor contains a thermally stable unreactive particulate solid heat exchange medium chosen from quartz sand, silicon dioxide, diatomaceous earth, kaolinite clay, montmorillonite-smectite clay, illite clay, chlorite clay, haematite, a zeolite, an acid treated char, an acid-treated activated carbon, a metal oxide, an acid-treated metal oxide, a metal sulfate, a metal phosphate, a metal carbonate, a metal-organic framework, and mixtures thereof.

12. The method according to claim 1 wherein the pyrolysis reactor comprises a fluidised bed reactor heated by fluidising gas passing through the fluidised bed, the fluidising gas comprising at least one of, oxygen-depleted air, nitrogen, steam, carbon dioxide, carbon monoxide, syngas and a substantially unreactive carrier gas and the pre-mix is subjected to at least one of preheating, dehydration, tumbling in an auger and steam injection prior to injection into the fluidised bed reactor.

13. The method according to claim 12 wherein the pyrolysis zone is maintained at pressure above 10 kPa.

14. The method according to claim 1 wherein the premix is given sufficient time to swell by absorbing the water and acid prior to being fed into the pyrolysis reactor.

15. Apparatus for producing levoglucosenone according to the method defined in claim 1 comprising,
- a dryer for receiving and reducing the water content of the cellulosic material and to deliver it by a first feeder to a mixer vessel for combining components of the pre-mix,
- a second feeder arranged to continuously transfer the pre-mix from the mixer vessel and to inject it into a pyrolysis zone of a fluidised bed pyrolysis reactor through a pre-mix inlet,
- a gas inlet configured to introduce a fluidising gas into a fluidised bed of thermally stable unreactive particulate solid in the pyrolysis reactor,
- a heater for maintaining the temperature in the fluidised bed within the range 250° C. to 450° C.,
- an outlet arranged to withdraw a gaseous stream containing entrained char solids from the pyrolysis reactor,
- a separator arranged to separate char solids from the gaseous stream, and
- at least one fractionating condenser assembly arranged to receive the separate gaseous stream from the separator to separately condense levoglucosenone and the solvent therefrom.

16. The apparatus according to claim 15 wherein the heating means comprises at least one of an electrical heating element, combustion means for combusting the separated char solids and a combination of these.

17. The apparatus according to claim 16 comprising a gasifier that converts the char into a gaseous mixture comprising nitrogen, carbon dioxide and carbon monoxide which are fed as the fluidising gas into the fluidised bed pyrolysis reactor.

* * * * *